US00PP30111P3

(12) United States Plant Patent
van Rijn

(10) Patent No.: US PP30,111 P3
(45) Date of Patent: Jan. 15, 2019

(54) ***ANTHURIUM* PLANT NAMED 'ARAANTBRO1'**

(50) Latin Name: ***Anthurium andraeanum* Linden ex Andre**
Varietal Denomination: ARAANTBRO1

(71) Applicant: J&D Horticulture B.V., De Lier (NL)

(72) Inventor: Silvia van Rijn, De Lier (NL)

(73) Assignee: J&D Horticulture B.V., De Lier (NL)

( * ) Notice: Subject to any disclaimer, the term of this patent is extended or adjusted under 35 U.S.C. 154(b) by 0 days.

(21) Appl. No.: 15/732,577

(22) Filed: Nov. 29, 2017

(65) Prior Publication Data

US 2018/0153078 P1 May 31, 2018

(30) Foreign Application Priority Data

Nov. 30, 2016 (QZ) ..... PBR 2016/2992

(51) Int. Cl.
*A01H 5/02* (2018.01)

(52) U.S. Cl.
USPC ..... Plt./365
CPC ..... *A01H 5/02* (2013.01)

(58) Field of Classification Search
USPC ..... Plt./365
See application file for complete search history.

*Primary Examiner* — Susan McCormick Ewoldt
(74) *Attorney, Agent, or Firm* — Samuel R. McCoy, Jr.

(57) ABSTRACT

'ARAANTBRO1' is a new and distinctive variety of *Anthurium* plant which is characterized by the combination of vigorous growth, a broad and upright habit, small dark green foliage, large dark brown spathes, and the stability of all characteristics from generation to generation. The new variety is typically produced as an indoor ornamental plant.

3 Drawing Sheets

Latin name of the genus and species: The Latin name of the genus and species of the novel variety disclosed herein is *Anthurium andraeanum* Linden ex Andre.

Variety denomination: The inventive variety of *Anthurium* disclosed herein has been given the variety denomination 'ARAANTBRO1'.

CROSS REFERENCE TO RELATED APPLICATIONS

This application claims priority to the Community Plant Variety Rights application number 2016/2992, filed Nov. 30, 2016, which is herein incorporated by reference.

BACKGROUND OF THE INVENTION

Parentage: The new cultivar is a seedling selection which resulted from the controlled pollination of *Anthurium andraeanum* 'K35' (not patented), the seed parent, and *Anthurium andraeanum* 'K36' (not patented), the pollen parent. Both parents are developed and owned by the inventor and were never commercially released. Said cross was performed by the inventor in De Lier, The Netherlands, in December of 2013. Seeds were harvested from 'K35', sown, and grown to maturity in order to evaluate for unique characteristics which may be of commercial value. In March of 2015, after evaluating the seedlings for approximately one year, one progeny was observed to exhibit small, dark green foliage with large, dark brown spathes. In April of 2015, after further evaluation to confirm the unique characteristics, the new cultivar was selected for commercialization and given the breeder denomination 'ARAANTBRO1'.

Asexual Reproduction: Asexual reproduction of 'ARAANTBRO1', by way of meristematic tissue culture, was first performed in April of 2015 at a laboratory in De Lier, the Netherlands. Three successive generations so produced have shown that the unique features of the instant cultivar are stable and reproduced true to type.

SUMMARY OF THE INVENTION

The cultivar 'ARAANTBRO1' has not been observed under all possible environmental conditions and the phenotype may vary somewhat with variations in the instant environment such as temperature, day length, and light intensity, without, however, any variance in genotype. The following characteristics have been repeatedly observed and represent the distinguishing characteristics of the new *Anthurium* cultivar 'ARAANTBRO1'. These traits, in combination, distinguish 'ARAANTBRO1' as a new and distinct cultivar.

1. *Anthurium* 'ARAANTBRO1' is a moderately vigorous herbaceous perennial with a broad, upright growth habit; and
2. *Anthurium* 'ARAANTBRO1' exhibits durable foliage and spathes; and
3. *Anthurium* 'ARAANTBRO1' exhibits small dark green foliage; and
4. *Anthurium* 'ARAANTBRO1' exhibits inflorescences with a large, dark brown spathe and a green spadix that is suffused with brown at the apex.

Figure 1:
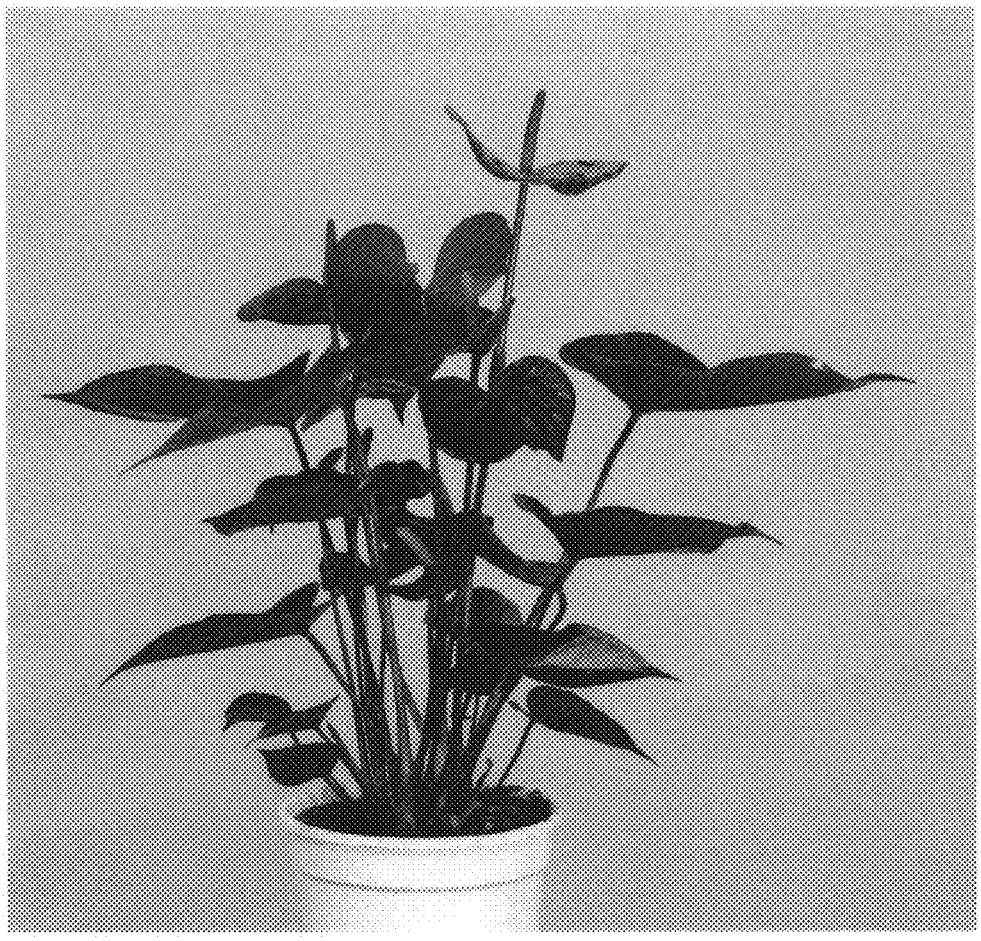
FIG. 1 shows, as nearly true as it is reasonably possible to make the same in color illustrations of this type, an exemplary plant of 'ARAANTBRO1', grown in a greenhouse in De Lier, the Netherlands. The plant shown is approximately 42 weeks old from a rooted cutting, potted into a 17 cm nursery pot.
Figure 2:
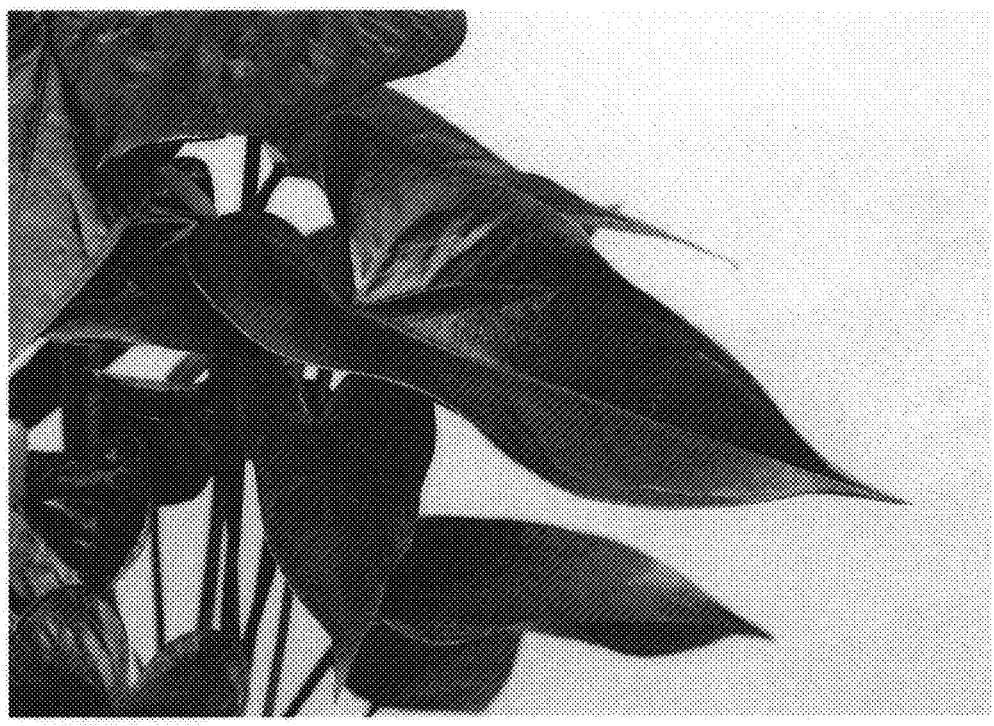
FIG. 2 shows, as nearly true as it is reasonably possible to make the same in color illustrations of this type, the typical foliage of 'ARAANTBRO1'.
Figure 3:
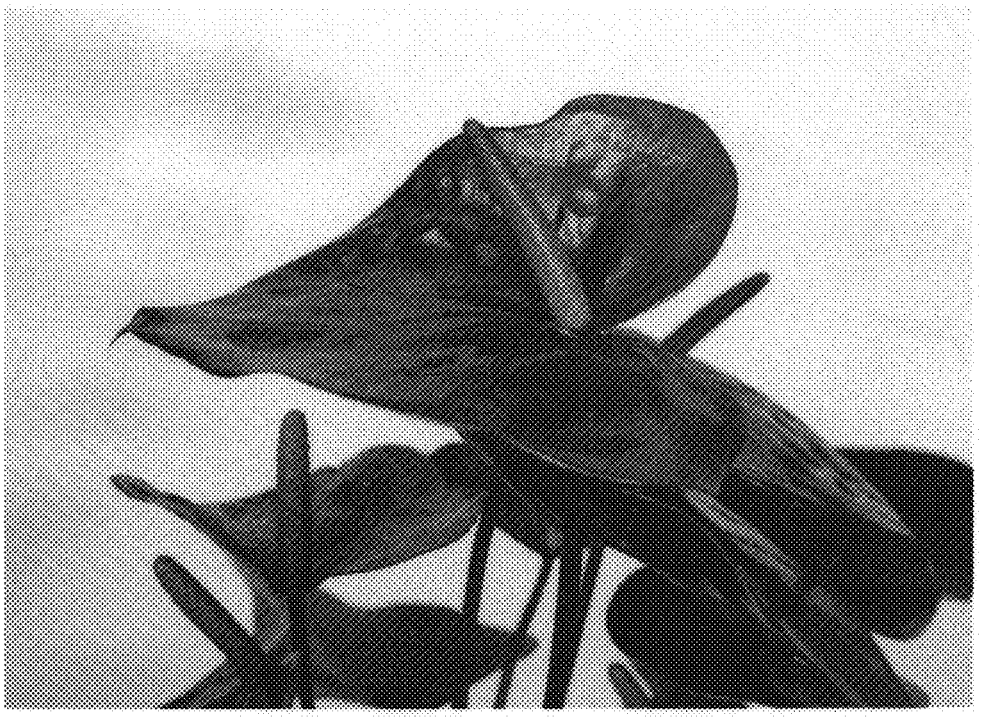
FIG. 3 shows, as nearly true as it is reasonably possible to make the same in color illustrations of this type, the typical inflorescence of 'ARAANTBRO1'.

The photographs were taken using conventional techniques and although colors may appear different from actual colors due to light reflectance it is as accurate as possible by conventional photographic techniques.

BOTANICAL DESCRIPTION OF THE PLANT

The following is a detailed botanical description of a new and distinct variety of *Anthurium* known as 'ARAANTBRO1', based upon observations made from a sample set of plants grown in 17 cm nursery pots which were approximately 42 weeks old from a rooted cutting. Plants were grown in a greenhouse in De Lier, The Netherlands, utilizing conventional greenhouse production protocols for *Anthurium*, which consisted of regular irrigation by way of ebb and flood watering benches and fertilizer applications of a complete fertilizer with micro nutrients at an EC value ranging from 1.0 to 1.8. No chemical pest or disease measures were utilized in production. Young plants are assimilated to the greenhouse under shade cloth and later move to light levels ranging from 3000 to 4000 lux for the final 5 months of production. Observation data was recorded in October of 2017.

Those skilled in the art will appreciate that certain characteristics will vary with older or, conversely, with younger plants. 'ARAANTBRO1' has not been observed under all possible environmental conditions. Where dimensions, sizes, colors and other characteristics are given, it is to be understood that such measurements are approximations or averages set forth as accurately as practicable. The phenotype of the variety may differ from the descriptions set forth herein with variations in environmental, climactic and cultural conditions. Color notations are based on *The Royal Horticultural Society Colour Chart*, The Royal Horticultural Society, London, sixth edition.

A botanical description of 'ARAANTBRO1' and comparisons with the parents and the most similar variety of common knowledge are provided below.

General plant description:

*Growth rate*.—Slow to moderately fast.

*Plant vigor*.—Moderately vigorous.

*Growth habit*.—Dioecious clump-forming, herbaceous perennial; broad upright.

*Plant shape*.—Broad obovate.

*Height*.—37.5 cm in height, to the highest leaf; 44.7 cm to top of the floral plane.

*Width*.—Average 43.7 cm in width.

*Propagation*.—Stem cuttings and meristematic tissue culture.

*Time to initiate roots*.—Approximately 30 days to initiate roots at approximately 23 degrees Centigrade.

*Time to produce a finished marketable plant*.—Approximately 60 weeks to produce a marketable plant in a 14 cm nursery pot.

*Environmental tolerances*.—Adapt to, at least, USDA Zones 10 to 13 and temperatures ranging from as high as 40 degrees Celsius and as low as 5 degrees Celsius; moderate to high tolerance to rain; low tolerance to wind.

*Pest resistance and susceptibility*.—Plants have not been observed to be susceptible or resistant to pathogens and pests common to *Anthurium*.

Root system:

*Root structure; texture*.—Not very dense; non-fibrous; moderately fleshy.

*Dimensions*.—Average length of 13.2 cm long and 0.3 cm in diameter.

*Color*.—Orange-red, nearest to a combination of RHS 35C and 35D.

Stems:

*Branching characteristics*.—Basally-branched plant with leaves growing in small clumps which form short lateral branches.

*Quantity of clumps per plant*.—3.

*Quantity of additional clumps per year*.—3.

*Lateral branches*.—Dimensions — 2.7 cm long and 1.1 cm in diameter. Attitude — Approximately 10 degrees from vertical. Cross-section — Round. Texture and luster — Smooth, glabrous, and moderately glossy. Strength — Strong. Color, juvenile — Yellow-green, nearest to RHS 145B. Color, mature — Yellow-green, nearest to RHS 144B. Color at internodes — Yellow-green, nearest to RHS 144B.

Foliage:

*Arrangement*.—Alternate.

*Division*.—Simple.

*Quantity of leaves per lateral branch*.—5 leaves per clump.

*Leaf shape*.—Cordate to narrow cordate.

*Leaf apex*.—Apiculate.

*Leaf base*.—Deeply cordate; lobes free.

*Aspect*.—Moderately to strongly concave.

*Leaf length*.—Average 20.4 cm in length.

*Leaf width*.—Average 10.1 cm in width.

*Leaf margin*.—Entire; slightly undulate.

*Texture and luster, adaxial surface*.—Smooth, glabrous and moderately glossy.

*Texture and luster, abaxial surface*.—Smooth, glabrous and glossy.

*Juvenile color, adaxial surface*.—Greyed-brown, nearest to RHS N199B.

*Juvenile color, abaxial surface*.—Greyed-brown, nearest to in between RHS N199A and N199B.

*Mature color, adaxial surface*.—Nearest to in between yellow-green, RHS 147A, and greyed-green, RHS N189A, but darker.

*Mature color, abaxial surface*.—Yellow-green, nearest to RHS 146A.

*Venation*.—Vein pattern — Pinnate. Vein color, adaxial surface — Yellow-green, nearest to RHS 147A. Vein color, abaxial surface — Yellow-green, nearest to RHS 146B.

*Petiole*.—Length — 23.4 cm, including the geniculum. Width — 0.4 cm. Texture and luster, both surfaces — Smooth, glabrous and moderately glossy. Color, adaxial surface — Yellow-green, nearest to in between RHS 146A and 147A. Color, abaxial surface — Yellow-green, nearest to RHS 146A but slightly darker. Strength — Very strong. Geniculum — Length — Approximately 3.6 cm. Width — Approximately 0.45 cm. Color — The upper surface is brown, nearest to RHS 200B; lower surface is green, nearest to RHS NN137B. Petiole wings — Length — Approximately 2.8 cm Width — Approximately 0.5 cm Color — Nearest to in between green, RHS NN137B, and yellow-green, RHS 147A, and darker towards the margins, nearest to RHS 143A; outer edge is suffused with greyed-purple, RHS 185B. Stipule — Occurrence — A dry stipule is present at the base of each petiole. Shape — Narrow oblong. Apex — Acute with a mucronate tip. Base — Broad cuneate. Dimensions — 5.5 cm long and 0.9 cm wide. Texture and luster, both surfaces — Smooth, glabrous, and matte. Color, both surfaces — Greyed-orange, nearest to in between RHS 165A and 165B.

Inflorescence:

*Type*.—Consisting of a spathe and spadix.

*Arrangement*.—Inflorescences are carried at or slightly above the leaf plane.

*Quantity per clump*.—3.

*Quantity per plant*.—9.

*Natural flowering season*.—Winter into spring.

*Height of spathe*.—5.4 cm.

*Time to flowering*.—13 weeks.

*Fragrance*.—Non fragrant.

*Self-cleaning or persistent*.—Persistent.

*Flower longevity*.—Flowers stay in good condition for approximately 4 weeks.

*Peduncle*.—Cross-section — Elliptical. Attitude — Approximately 15 degrees to the lateral branch axis. Length — Approximately 29.1 cm. Diameter — Approximately 0.5 cm. Texture and luster, both surfaces — Smooth, glabrous, and glossy. Color — Yellow-green, nearest to RHS 146A but darker, and fading lighter towards the proximal end, nearest to RHS 144A; fading to brown towards the distal end, nearest to RHS 200B. Strength — Strong.

Spathe:

*Attitude*.—Approximately 20 degrees to horizontal; apex pointed slightly downward at an average angle of 20 degrees to the spathe.

*Length*.—Approximately 12.4 cm.

*Width*.—Approximately 11.4 cm.

*Shape*.—Broad cordate.

*Aspect*.—Flat to slightly concave.

*Margin*.—Entire; lightly undulated.

*Apex*.—Short apiculate with a mucronate tip.

*Base*.—Cordate.

*Texture and luster, upper surface*.—Rugose, glabrous, and very glossy.

*Texture and luster, lower surface*.—Rugose, glabrous, and very glossy.

*Color*.—Upper surface, when opening — Nearest to in between greyed-red, a mixture of RHS 183A and N186C, and brown, RHS 200A; fading to greyed-brown towards the base, nearest to in between RHS N199A and N199B. Lower surface, when opening — Nearest to in between greyed-orange, RHS 165A, and greyed-brown, RHS N199B; fading to greyed-brown towards the base, nearest to in between RHS 199A and N199C. Upper surface, when fully opened — Brown, nearest to a mixture of RHS 200A and 200B, and lightly suffused with a reddish coloration (R.H.S. color designations cannot be determined); suffused with a mixture of green and yellow-green towards the base, nearest to RHS NN137A and 147A but slightly darker; outer tip is green, nearest to RHS 143A. Lower surface, when fully opened — A mixture of greyed-brown, nearest to RHS N199A and N199B, and brown, RHS 200D; suffused with yellow-green, nearest to RHS 148A; outer tip is green, nearest to RHS 143A. Venation on the upper surface, when fully opened — Brown, nearest to RHS 200B. Venation on the lower surface, when fully opened — Greyed-orange, nearest to RHS 175A but slightly darker. Upper surface when fading — Brown, nearest to RHS 200A, and lightly suffused with a reddish coloration (R.H.S. color designations cannot be determined); suffused with yellow-green towards the base, nearest to RHS 147A; outer tip is green, nearest to RHS 143A. Lower surface when fading — Greyed-red, nearest to RHS 178A, and fading to yellow-green towards the base, nearest to in between RHS 146A and 146B.

Spadix:

*Attitude*.—Approximately 65 degrees to the spathe.

*Shape*.—Cylindrical.

*Apex*.—Obtuse.

*Base*.—Obtuse.

*Length*.—Approximately 5.3 cm.

*Width*.—Approximately 0.85 cm.

*Texture and luster*.—Smooth, glabrous, and moderately glossy.

*Color*.—When opening — Yellow-green, nearest to in between RHS 144A and 146B; tip is greyed-brown, nearest to RHS N199B. When fully opened — Yellow-green, nearest to RHS 146B; tip is brown, nearest to RHS N200B. When fading — Yellow-green, nearest to RHS 146C; tip is lighter, nearest to RHS 153C.

*Quantity of flowers per spadix*.—Approximately 300.

*Spadix flower arrangement*.—Rotate.

*Spadix flower shape*.—Flattened; rotate.

*Spadix flower diameter*.—Approximately 2.5 mm.

*Spadix flower depth*.—Approximately 0.75 mm.

Reproductive organs:

*Androecium*.—None detected.

*Gynoecium*.—Pistil quantity — One. Length — 0.5 mm. Stigma — Shape — Club-shaped. Dimensions — Approximately 0.3 mm across and 0.15 mm tall. Color — Yellow-green, nearest to RHS 148D. Style — Length — 0.3 mm. Color — Green; R.H.S. color designations cannot be determined due to the minute nature of the filament. Ovary — Color — Green, nearest to RHS 143A.

Seed and fruit: Seed production has not been observed.

COMPARISONS WITH THE PARENT

Plants of the new cultivar 'ARAANTBRO1' differ from the seed parent, *Anthurium* 'K35' (not patented), in the following characteristics described in Table 1 below.

TABLE 1

| Characteristic | 'ARAANTBRO1' | 'K35' |
|---|---|---|
| General coloration of the mature foliage. | Darker green. | Lighter green. |
| Size of the mature foliage. | Smaller than 'K35'. | Larger than 'ARAANTBRO1'. |
| Spathe size. | Larger than 'K35'. | Smaller than 'ARAANTBRO1'. |
| Spathe shape. | Broad cordate; more rounded than 'K35'. | Cordate; narrower than 'ARAANTBRO1'. |

Plants of the new cultivar 'ARAANTBRO1' may be distinguished from the pollen parent, 'K36', by the following combination of characteristics described in Table 2 below.

TABLE 2

| Characteristic | 'ARAANTBRO1' | 'K36' |
|---|---|---|
| General coloration of the mature foliage. | Darker green. | Lighter green. |
| Size of the mature foliage. | Smaller than 'K36'. | Larger than 'ARAANTBRO1'. |
| Spathe size. | Larger than 'K36'. | Smaller than 'ARAANTBRO1'. |

COMPARISONS WITH THE MOST SIMILAR VARIETY OF COMMON KNOWLEDGE

Plants of the new cultivar 'ARAANTBRO1' differ from the commercial variety, *Anthurium* 'Giant Chocolate' (not patented), in the following characteristics described in Table 3 below.

TABLE 3

| Characteristic | 'ARAANTBRO1' | 'Giant Chocolate' |
|---|---|---|
| Growth habit. | More compact than 'Giant Chocolate'. | Less compact than 'ARAANTBRO1'. |
| Size of the mature foliage. | Smaller than 'Giant Chocolate'. | Larger than 'ARAANTBRO1'. |
| Leaf apex. | Apiculate. | Broad apiculate. |
| Spathe apex. | Short apiculate with a mucronate tip. | Broadly mucronate. |
| General coloration of the base of the spathe. | Margins are more heavily suffused with green. | Margins are lightly suffused with green. |

That which is claimed is:

1. A new and distinct variety of *Anthurium* plant named 'ARAANTBRO1', substantially as described and illustrated herein.

* * * * *